(12) United States Patent
Sohn et al.

(10) Patent No.: US 9,353,222 B2
(45) Date of Patent: May 31, 2016

(54) COMPOSITION, POLYMER FILM, AND DISPLAY DEVICE

(71) Applicant: SAMSUNG ELECTRONICS CO., LTD., Suwon-si, Gyeonggi-do (KR)

(72) Inventors: Byung Hee Sohn, Yongin-si (KR); Yoon Seok Ko, Seoul (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 0 days.

(21) Appl. No.: 14/197,378

(22) Filed: Mar. 5, 2014

(65) Prior Publication Data

US 2015/0025200 A1   Jan. 22, 2015

(30) Foreign Application Priority Data

Jul. 19, 2013   (KR) .......................... 10-2013-0085514

(51) Int. Cl.

| C08G 73/00 | (2006.01) |
|---|---|
| C08G 73/10 | (2006.01) |
| C07D 307/89 | (2006.01) |
| G03F 7/037 | (2006.01) |
| C08J 5/18 | (2006.01) |
| C07D 213/38 | (2006.01) |

(52) U.S. Cl.
CPC .......... *C08G 73/1007* (2013.01); *C07D 213/38* (2013.01); *C08G 73/1085* (2013.01); *C08J 5/18* (2013.01); *C08J 2379/08* (2013.01)

(58) Field of Classification Search
None
See application file for complete search history.

(56) References Cited

U.S. PATENT DOCUMENTS

| 4,959,151 A * | 9/1990 | Nakatani et al. .............. 210/640 |
|---|---|---|
| 6,329,494 B1 | 12/2001 | Arai et al. |
| 6,600,053 B2 | 7/2003 | Arai et al. |
| 2002/0037991 A1 | 3/2002 | Arai et al. |

FOREIGN PATENT DOCUMENTS

| CN | 101787129 A | 7/2010 |
|---|---|---|
| EP | 1013650 B1 | 1/2007 |
| JP | 2002363283 A | 12/2002 |

OTHER PUBLICATIONS

Frank W Harris, et al., "Organo-soluble polyimides: synthesis and characterization of polyimides containing phenylated p-biphenyl and p-terphenyl units," High Performance Polymers (1997), 9(3), pp. 251-261.

* cited by examiner

*Primary Examiner* — Ana Woodward
(74) *Attorney, Agent, or Firm* — Cantor Colburn LLP

(57) ABSTRACT

A composition including a diamine compound and a dianhydride compound, wherein the diamine compound includes a first diamine compound represented by Chemical Formula 1, Chemical Formula 1

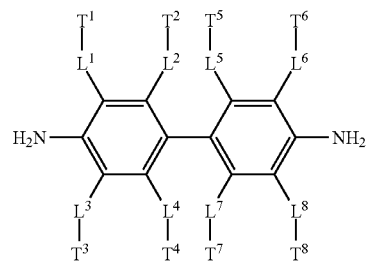

wherein, in Chemical Formula 1, $T^1$ to $T^8$ and $L^1$ to $L^8$ are the same as defined in the detailed description.

14 Claims, 2 Drawing Sheets

COMPOSITION, POLYMER FILM, AND DISPLAY DEVICE

This application claims priority to Korean Patent Application No. 10-2013-0085514, filed on Jul. 19, 2013, and all the benefits accruing therefrom under 35 U.S.C. §119, the content of which is incorporated herein in its entirety by reference.

BACKGROUND

1. Field

A composition, a polymer film, and a display device are disclosed herein.

2. Description of the Related Art

As informatization has grown, there has been an increasing demand for display devices that consume a small amount of power, that are light and flexible like paper, and that can be used anywhere and at any time as a display for visualizing a large volume of information and delivering it to people. The flexible display device complicatedly requires a flexible substrate, organic and inorganic materials for a low temperature process, flexible electronics, and sealing and packing technology. The flexible substrate is an important part for determining performance, reliability, and price of the flexible display device.

A polymer substrate may be useful as the flexible substrate, since it is light, easy to manufacture, and can be produced through a continuous process.

However, the polymer substrate essentially has low heat resistance, and therefore, there remains a need in a polymer substrate having improved properties for its substantial application, and increased transparency to satisfy characteristics of a substrate for a display device.

SUMMARY

An embodiment provides a composition including a diamine compound capable of improving transparency and increasing heat resistance.

Another embodiment provides a polymer film including a polymer obtained by polymerizing the composition.

Yet another embodiment provides a display device including the polymer film.

Still another embodiment provides a novel diamine compound.

According to an embodiment, a composition including a diamine compound and dianhydride compound is provided, wherein the diamine compound includes a first diamine compound represented by Chemical Formula 1.

Chemical Formula 1

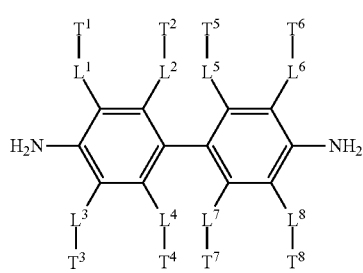

In Chemical Formula 1, $T^1$ to $T^8$ are independently hydrogen, a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C2 to C30 heteroaryl group, or a combination thereof, at least one of $T^1$ to $T^8$ is a substituted or unsubstituted C2 to C30 heteroaryl group, and $L^1$ to $L^8$ are independently a single bond, a substituted or unsubstituted C1 to C20 alkylene group, a substituted or unsubstituted C3 to C20 cycloalkylene group, a substituted or unsubstituted C2 to C30 heterocycloalkylene group, a substituted or unsubstituted C6 to C30 arylene group, a substituted or unsubstituted C2 to C30 heteroarylene group, $-SiR^aR^b-$, $-(Si=O)_p-$, $-NR^cR^d-$, or a combination thereof, wherein $R^a$ to $R^d$ are each independently hydrogen or a substituted or unsubstituted C1 to C20 alkyl group, and p is 1 to 20.

The first diamine compound may be a compound represented by Chemical Formula 2.

Chemical Formula 2

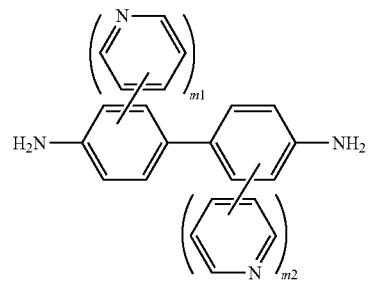

In Chemical Formula 2, m1 and m2 are each independently 0 or 1, provided that m1 and m2 are not simultaneously 0.

The first diamine compound may include at least one of compounds listed in Group 1.

Group 1

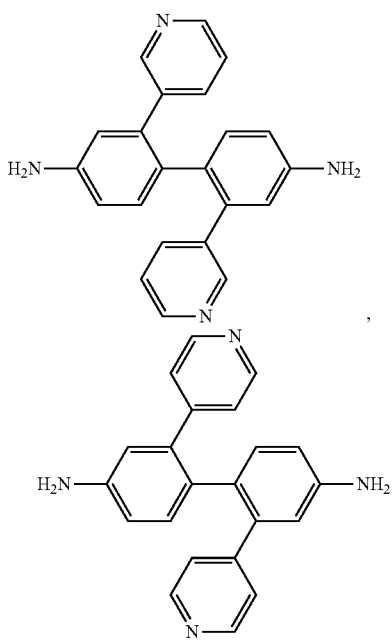

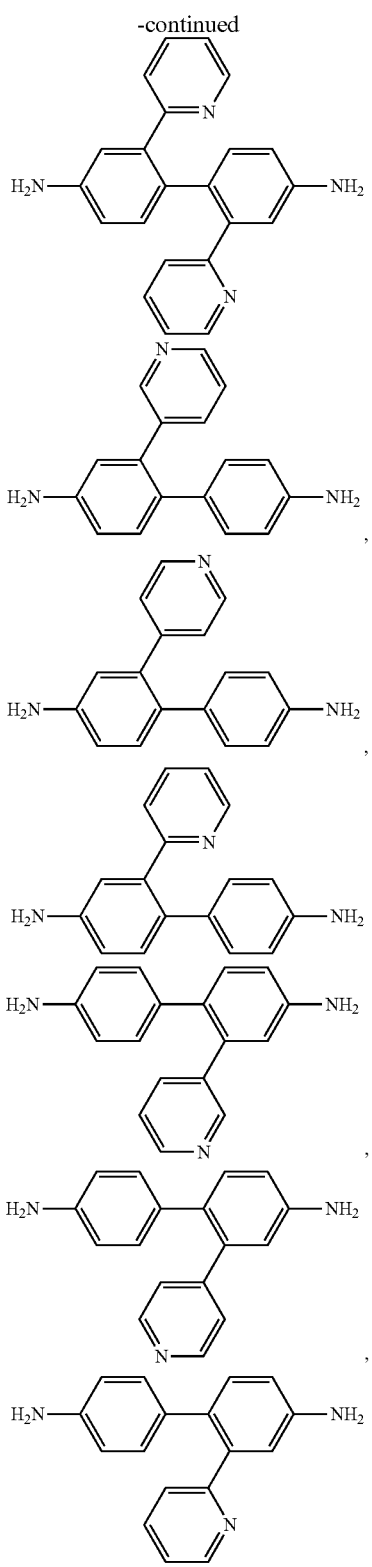

The diamine compound may further include a second diamine compound that is different from the first diamine compound.

The first diamine compound may be included in a ratio of about 0.01 to about 1 mole based on a total of 1 mole of the dianhydride compound.

The first diamine compound may be included in a ratio of about 0.01 to 0.4 moles based on a total of 1 mole of the dianhydride compound.

According to another embodiment, a polymer film including a polymer, wherein the polymer is a polymerization product of the composition is provided.

The polymer may be a polyamic acid, a polyimide, or a combination thereof.

The polymer may include a repeating unit represented by Chemical Formula 3, a repeating unit represented by Chemical Formula 4, or a combination thereof.

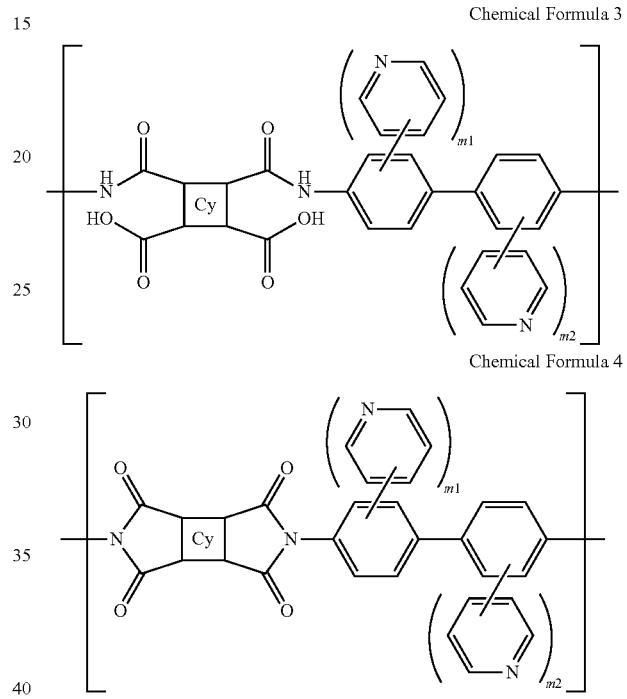

Chemical Formula 3

Chemical Formula 4

In Chemical Formula 3 or 4,

Cy is a group including a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C3 to C20 heteroaryl group, or a combination thereof, m1 and m2 are each independently 0 or 1, provided that m1 and m2 are not simultaneously 0.

According to yet another embodiment, a display device including the polymer film is provided.

The polymer film may be a substrate.

The display device may further include a thin film transistor, a liquid crystal device, an organic light emitting diode, or a combination thereof that are disposed on one side of the polymer film.

According to still another embodiment, a diamine compound represented by Chemical Formula 1 is provided.

The diamine compound may be represented by Chemical Formula 2.

The diamine compound may include at least one of the compounds listed in the Group 1.

The second diamine compound may be represented by Chemical Formula 5.

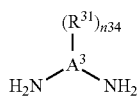

Chemical Formula 5

In Chemical Formula 5, $A^3$ is a substituted or unsubstituted group derived from a C1 to C20 alkane, a C6 to C30 arene, a C3 to C30 heteroarene, a C3 to C30 cycloalkane, a C3 to C30 heterocycloalkane, or a combination thereof, $R^{31}$ is hydrogen, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C2 to C15 heteroaryl group, or a combination thereof, $n^{34}$ is an integer ranging from 0 to 10, provided that n34+2 is equal to the bond valency of $A^3$.

The second diamine compound may be at least one selected from compounds represented by Group 2.

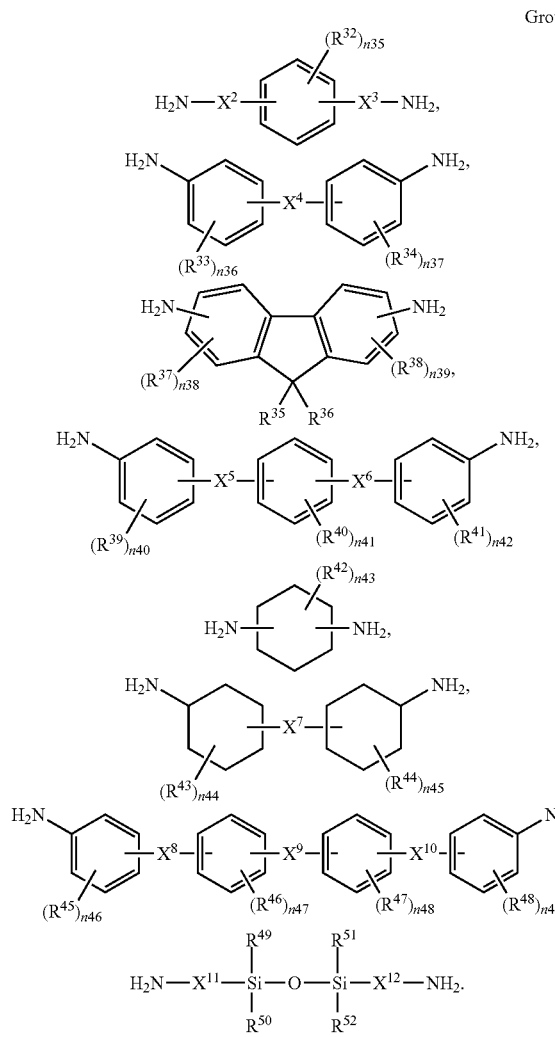

Group 2

In Group 2, $R^{32}$ to $R^{52}$ are each independently hydrogen, a halogen atom, a nitro group, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C2 to C20 heteroaryl group, or a combination thereof, and $X^2$ to $X^{12}$ are each independently a single bond, a substituted or unsubstituted C1 to C20 alkylene group, a substituted or unsubstituted C3 to C20 cycloalkylene group, a substituted or unsubstituted C6 to C20 arylene group, —SO$_2$—, —O—, —C(=O)—, or a combination thereof.

The second diamine compound is at least one selected from the compounds represented by Group 3.

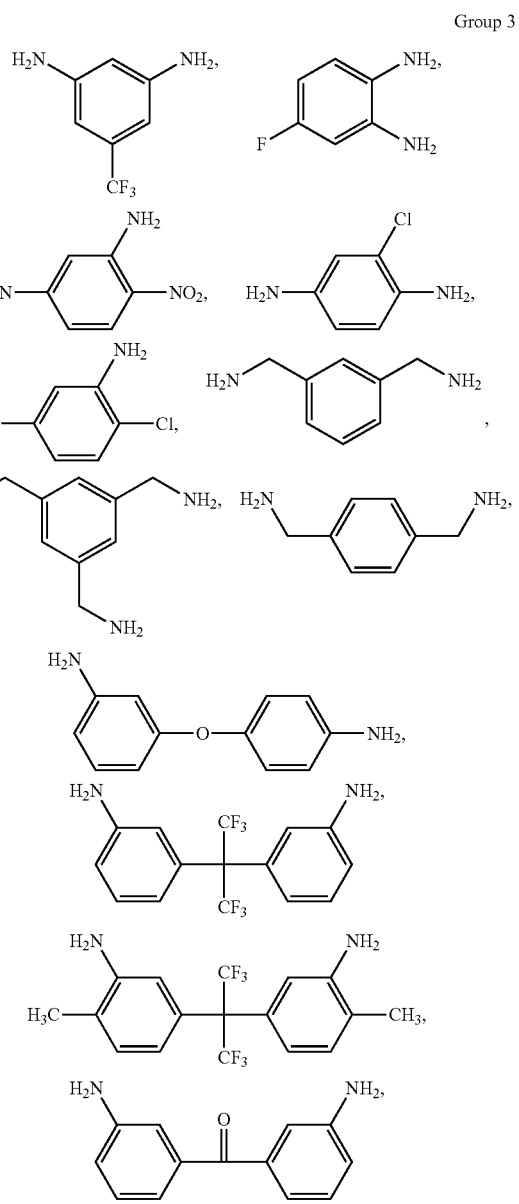

Group 3

-continued

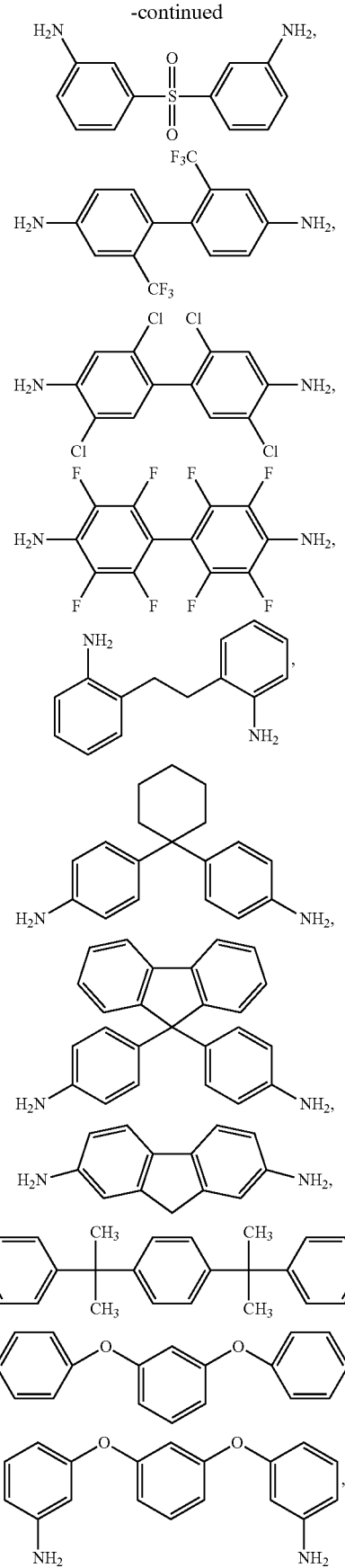

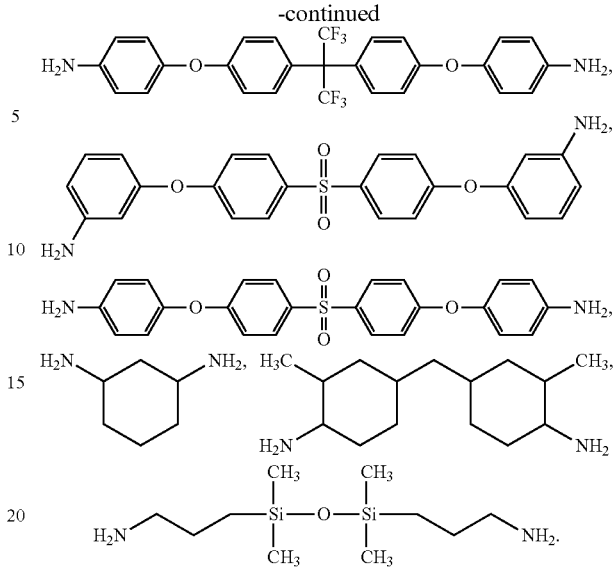

The dianhydride compound may be represented by Chemical Formula 6.

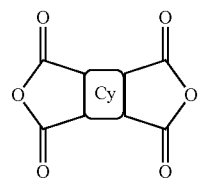

Chemical Formula 6

In Chemical Formula 6,

Cy is a moiety including a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C3 to C20 heteroaryl group, or a combination thereof.

The dianhydride compound may be at least one selected from 3,3',4,4'-biphenyl tetracarboxylic dianhydride, bicyclic [2.2.2]oct-7-ene-2,3,5,6-tetracarboxylic dianhydride, 3,3',4,4'-diphenylsulfone tetracarboxylic dianhydride, 4,4'-(hexafluoroisopropylidene)diphthalic anhydride, 4,4'-oxydiphthalic anhydride, pyromellitic dianhydride, and 4-(2,5-dioxotetrahydrofuran-3-yl)-1,2,3,4-tetrahydronaphthalene-1,2-dicarboxylic anhydride.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
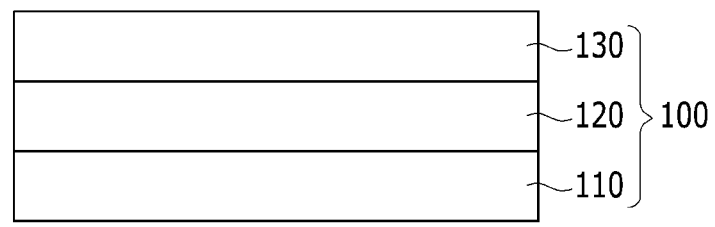
FIG. 1 is a cross-sectional view showing a liquid crystal display ("LCD") according to an embodiment.

Exemplary embodiments will hereinafter be described in detail, and may be easily performed by those who have common knowledge in the related art. However, this disclosure may be embodied in many different forms, and is not construed as limited to the exemplary embodiments set forth herein, but rather is defined by the scope of the appended claims.

Accordingly, the embodiments are merely described below, by referring to the figures, to explain aspects of the present description. As used herein, the term "and/or" includes any and all combinations of one or more of the associated listed items. The term "or" means "and/or." Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Additional aspects will be set forth in part in the description which follows and, in part, will be apparent from the description.

As used herein, when a definition is not otherwise provided, the term "substituted" refers to a compound or group substituted with a substituent selected from a halogen atom (—F, —Br, —Cl, or —I), a hydroxy group, a C1 to C20 alkoxy group, a cyano group, an amino group (—NH$_2$, —NH(R$^{100}$) or —N(R$^{101}$)(R$^{102}$), wherein R$^{100}$, R$^{101}$, and R$^{102}$ are the same or different and may independently be a C1 to C10 alkylamino group, an amidino group, a hydrazine group, a hydrazone group, a carboxyl group, a C1 to C20 ester group, a ketone group, a C1 to C20 alkyl group, a C2 to C20 alkenyl group, a C2 to C20 alkynyl group, a C1 to C20 aryl group, a C1 to C20 heteroaryl group, and a combination thereof, instead of hydrogen of a compound.

As used herein, when a definition is not otherwise provided, the term "hetero" refers to a functional group including 1 to 3 heteroatoms selected from N, O, S, and P.

As used herein, the term "alkyl group" refers to a straight or branched chain saturated aliphatic hydrocarbon having the specified number of carbon atoms. Non-limiting examples of the alkyl group are methyl and ethyl.

As used herein, the term "cycloalkyl group" refers to a group having one or more saturated rings in which all ring members are carbon. Non-limiting examples of the cycloalkyl group are cyclopentyl and cyclohexyl.

As used herein, the term "heterocycloalkyl group" refers to a saturated cyclic group containing from 1 to about 3 heteroatoms chosen from N, O, and S, with remaining ring atoms being carbon. Non-limiting example of the heterocycloalkyl group is 2-tetrahydropyranyl.

As used herein, the term "aryl group" refers to an aromatic group containing only carbon in the aromatic ring or rings. Non-limiting examples of the aryl group are phenyl and naphthyl.

As used herein, the term "heteroaryl group" refers to a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. Non-limiting examples of the heteroaryl group are 2-pyridyl and 2-imidazolyl.

As used herein, the term "alkylene group" refers to a straight or branched chain, saturated, divalent aliphatic hydrocarbon group. Non-limiting examples of the alkylene group are methylene and ethylene.

As used herein, the term "alkylene group" refers to a straight or branched chain, saturated, divalent aliphatic hydrocarbon group. Non-limiting examples of the alkylene group are methylene and ethylene.

As used herein, the term "cycloalkylene group" refers to a divalent radical formed by the removal of two hydrogen atoms from one or more rings of a cycloalkyl group. Non-limiting examples of the cycloalkylene group are cyclopentylene and cyclohexylene.

As used herein, the term "arylene group" refers to a divalent group formed by the removal of two hydrogen atoms from one or more rings of an arene, wherein the hydrogen atoms may be removed from the same or different rings. Non-limiting examples of the arylene group are phenylene and naphthylene.

As used herein, the term "heterocycloalkylene group" refers to a divalent saturated cyclic group containing from 1 to about 3 heteroatoms chosen from N, O, and S, with remaining ring atoms being carbon. Non-limiting example of the heterocycloalkyl group is 2,6-tetrahydropyranylene.

As used herein, the term "heteroarylene group" refers to a stable divalent 5- to 7-membered monocyclic or 7- to 10-membered bicyclic heterocyclic group which contains at least 1 aromatic ring that contains from 1 to 4, or preferably from 1 to 3, heteroatoms chosen from N, O, and S, with remaining ring atoms being carbon. Non-limiting examples of the heteroaryl group are 2,6-pyridylene and 2,4-imidazolylene.

Hereinafter, a novel diamine compound according to an embodiment is described.

According to an embodiment, a novel diamine compound including an aromatic group substituted with at least one heteroaryl group is provided.

The diamine compound may be represented by the following Chemical Formula 1.

Chemical Formula 1

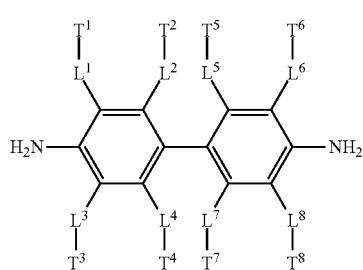

In the above Chemical Formula 1, $T^1$ to $T^8$ are independently hydrogen, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C1 to C30 aryl group, a substituted or unsubstituted heteroaryl group, or a combination thereof, at least one of $T^1$ to $T^8$ is a substituted or unsubstituted C2 to C30 heteroaryl group, and $L^1$ to $L^8$ are independently a single bond, a substituted or unsubstituted C1 to C20 alkylene group, a substituted or unsubstituted C3 to C20 arylene group, $SiR^aR^b$, $(Si-O)_p$, $NR^cR^d$, or a combination thereof, wherein $R^a$ to $R^d$ are each independently hydrogen or a substituted or unsubstituted C1 to C20 alkyl group, and p is 1 to 20.

The diamine compound may be, for example, represented by the following Chemical Formula 2.

Chemical Formula 2

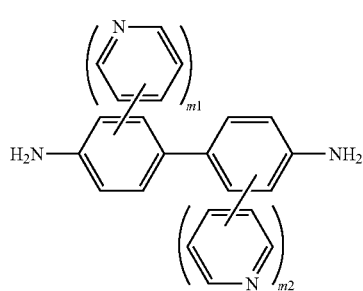

In the above Chemical Formula 2,
m1 and m2 are each independently 0 or 1, provided that m1 and m are not simultaneously 0.

The first diamine compound may include at least one of the compounds listed in the following Group 1.

Group 1

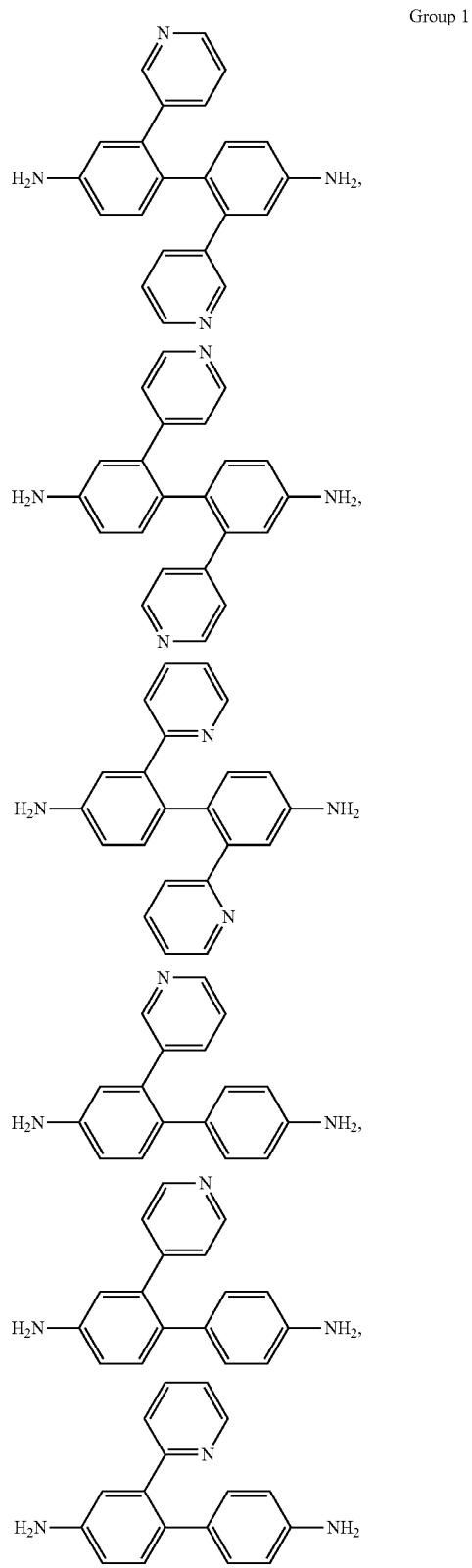

-continued

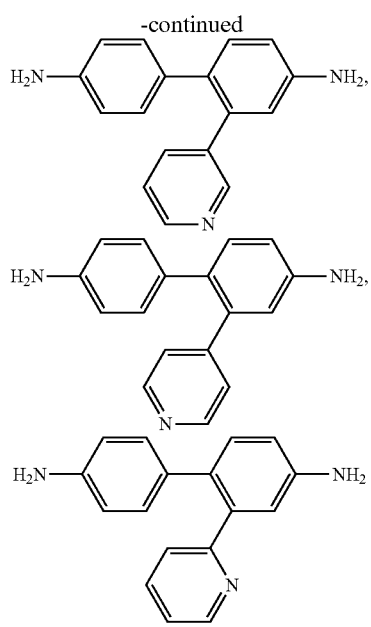

The diamine compound may be used as a monomer for forming a polyimide.

Hereinafter, a composition for forming a polyimide is described.

A composition according to an embodiment includes a diamine compound and a dianhydride compound, wherein the diamine compound includes a first diamine compound having an aromatic group substituted with at least one heteroaryl group.

The first diamine compound may be represented by the following Chemical Formula 1.

Chemical Formula 1

$$\begin{array}{c} T^1 \quad T^2 \quad T^5 \quad T^6 \\ | \quad | \quad | \quad | \\ L^1 \quad L^2 \quad L^5 \quad L^6 \\ H_2N - \phantom{xxxxxxx} - NH_2 \\ L^3 \quad L^4 \quad L^7 \quad L^8 \\ | \quad | \quad | \quad | \\ T^3 \quad T^4 \quad T^7 \quad T^8 \end{array}$$

In the above Chemical Formula 1, $T^1$ to $T^8$ are independently hydrogen, a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C2 to C30 heteroaryl group, or a combination thereof, at least one of $T^1$ to $T^8$ is a substituted or unsubstituted C2 to C30 heteroaryl group, and $L^1$ to $L^8$ are independently a single bond, a substituted or unsubstituted C1 to C20 alkylene group, a substituted or unsubstituted C3 to C20 cycloalkylene group, a substituted or unsubstituted C2 to C30 heterocycloalkylene group, a substituted or unsubstituted C6 to C30 arylene group, a substituted or unsubstituted C2 to C30 heteroarylene group, —SiR$^a$R$^b$—, —(Si=O)$_p$—, —NR$^c$R$^d$—, or a combination thereof, wherein R$^a$ to R$^d$ are each independently hydrogen or a substituted or unsubstituted C1 to C20 alkyl group, and p is 1 to 20.

The first diamine compound may be, for example, a compound represented by the following Chemical Formula 2.

Chemical Formula 2

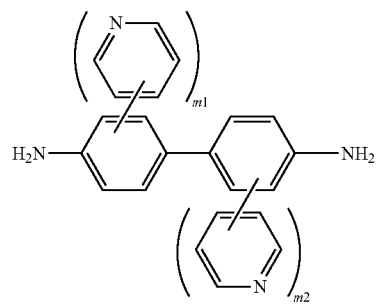

In the above Chemical Formula 2, m1 and m2 are each independently 0 or 1, provided that m1 and m2 are not simultaneously 0.

The first diamine compound may include, for example at least one of the compounds listed in the following Group 1.

Group 1

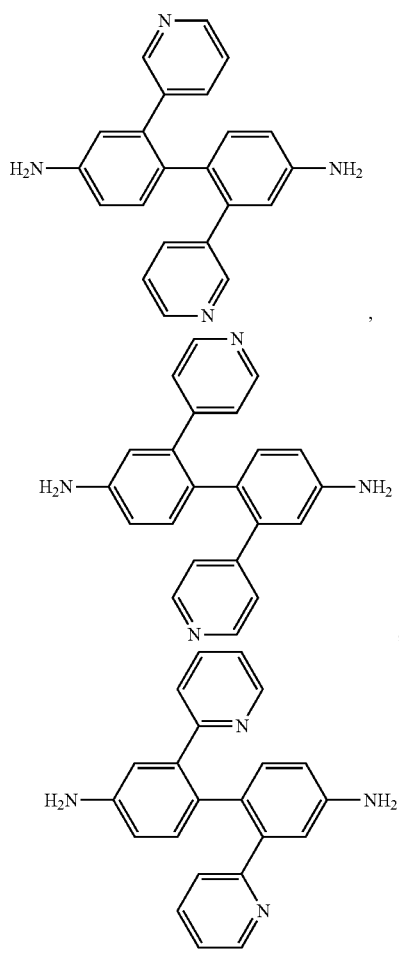

-continued

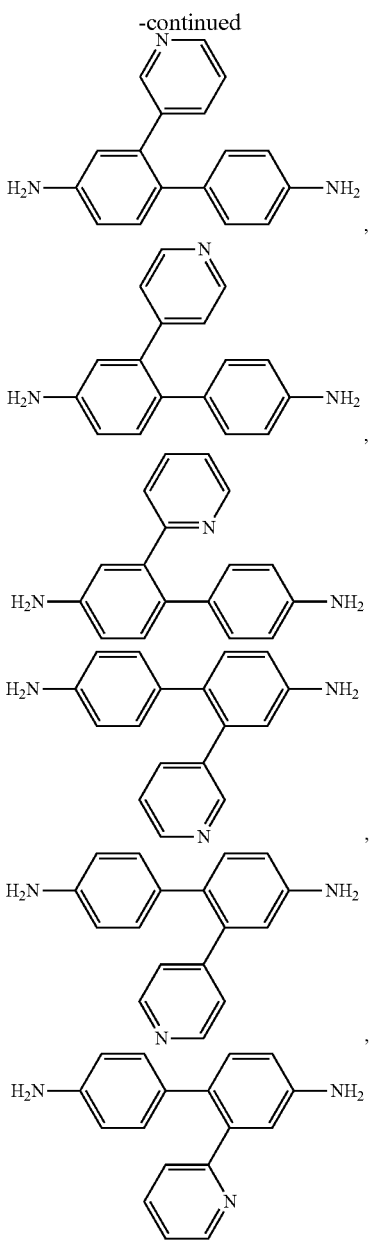

Since the first diamine compound has at least one heteroaryl group at the side chain, and heteroatoms of the heteroaryl group form a secondary bond such as a van der Waals bond with neighboring molecules or elements of a polymer, thermal motion of the polymer may be controlled. Accordingly, thermal stability is increased, while shrinkage/expansion caused by heat is decreased.

In addition, the first diamine compound has at least one heteroaryl group at the side chain, forming a bulky side chain. Such a bulky side chain may hinder stacking among molecules, decrease a charge transfer ("CT") complex, and thus improve photo-transmittance in a short wavelength region. Accordingly, transparency of a polymer obtained from a composition including the first diamine compound may be improved.

The first diamine compound may be used singularly or as a mixture of two or more compounds.

The diamine compound may further include a second diamine compound that is different from the first diamine compound.

The second diamine compound may be, for example represented by the following Chemical Formula 5.

Chemical Formula 5

In the above Chemical Formula 5, $A^3$ is a substituted or unsubstituted group derived from a C1 to C20 alkane, a C6 to C30 arene, a C3 to C30 heteroarene, a C3 to C30 cycloalkane, a C3 to C30 heterocycloalkane, or a combination thereof, $R^{31}$ is hydrogen, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C2 to C15 heteroaryl group, or a combination thereof, $n^{34}$ is an integer ranging from 0 to 10, provided that $n34+2$ is equal to the bond valency of $A^3$.

The second diamine compound may be, for example, selected from the compounds listed in Group 2, but is not limited thereto.

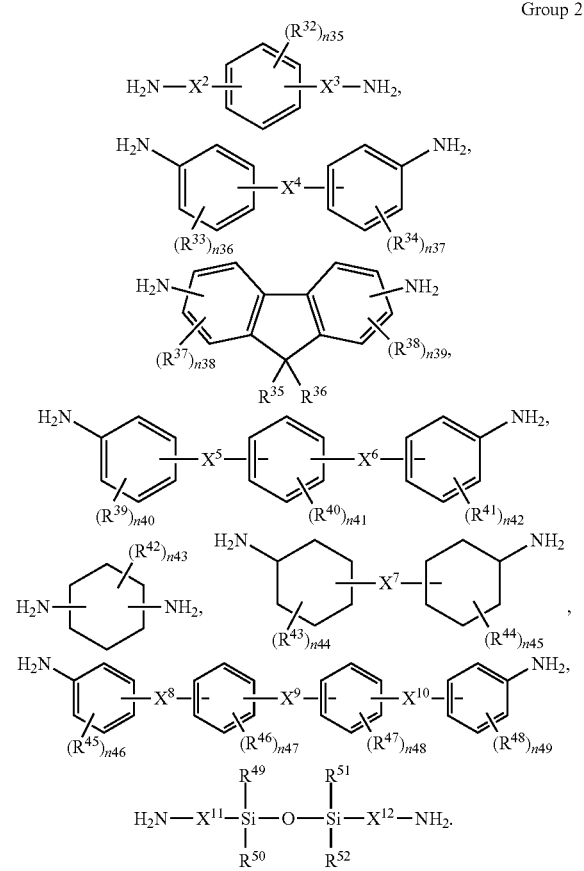

Group 2

In Group 2, $R^{32}$ to $R^{52}$ are each independently hydrogen, a halogen atom, a nitro group, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C2 to C20 heteroaryl group, or a combination thereof, and $X^2$ to $X^{12}$ are each independently a single bond, a substituted or unsubstituted C1 to C20 alkylene group, a substituted or unsubstituted C3 to C20 cycloalkylene group, a substituted or unsubstituted C6 to C20 arylene group, —SO$_2$—, —O—, —C(=O)—, or a combination thereof.

In an embodiment, the second diamine compound may be, for example, selected from the compounds listed in the following Group 3, but is not limited thereto.

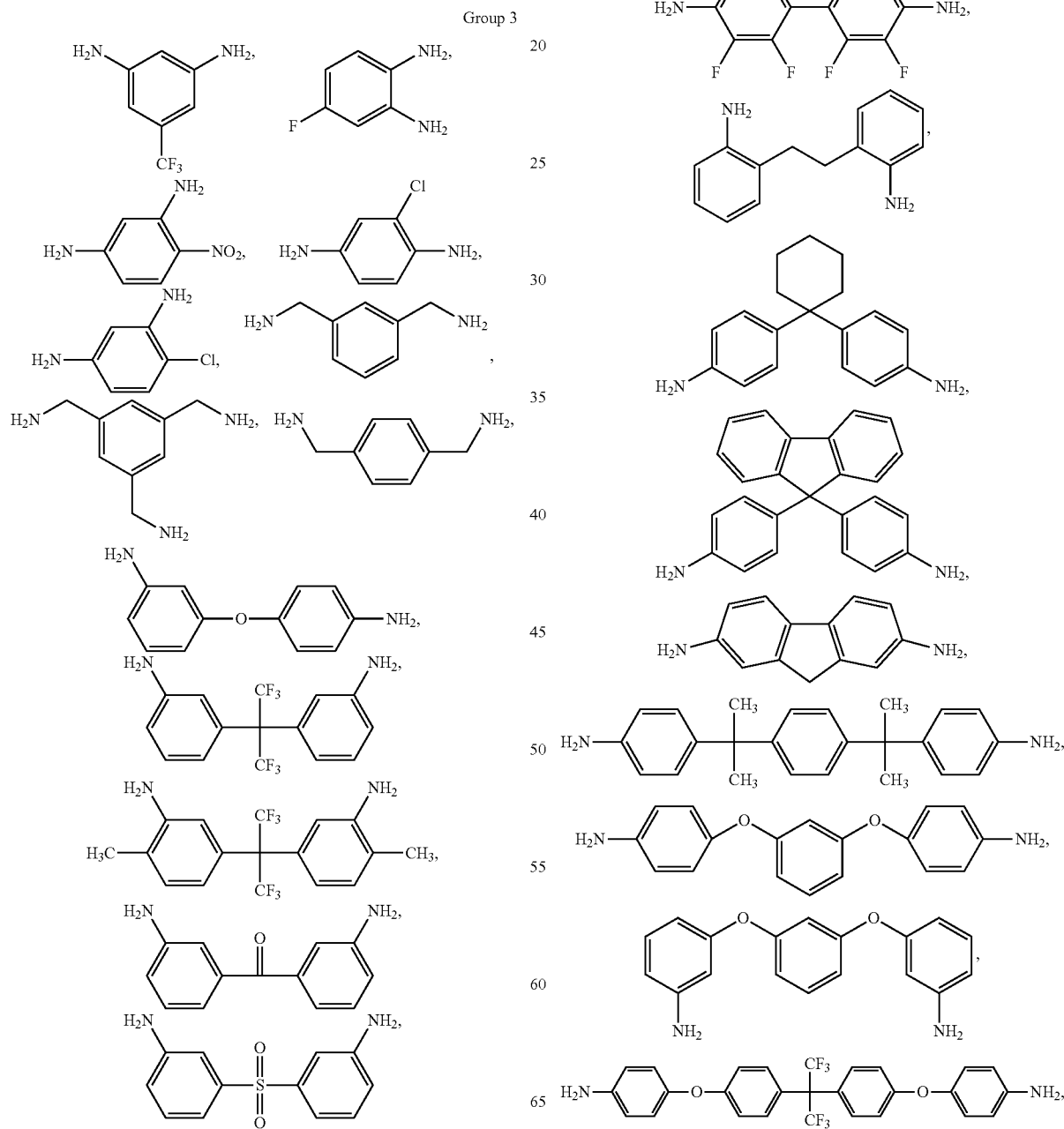

Group 3

-continued

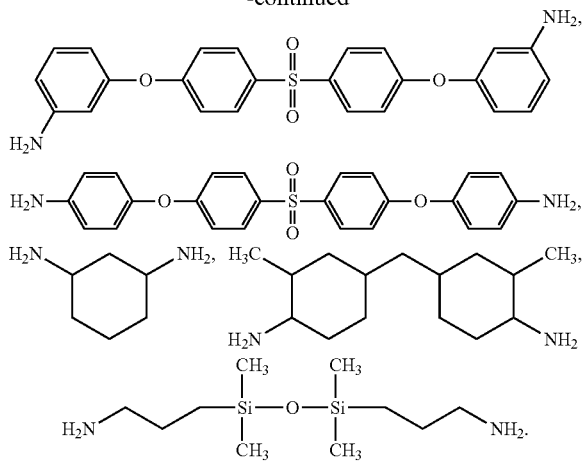

The dianhydride compound may be, for example represented by the following Chemical Formula 6.

Chemical Formula 6

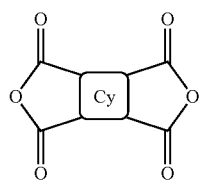

In the above Chemical Formula 6,

Cy is a moiety including a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C3 to C20 heteroaryl group, or a combination thereof.

The Cy may be, for example, a substituted or unsubstituted C6 to C20 monocyclic aryl group, a substituted or unsubstituted C6 to C20 condensed polycyclic aryl group, a C6 to C20 non-condensed polycyclic aryl group linked by a substituted or unsubstituted aryl group to each other, or a combination thereof.

The dianhydride compound may be, for example 3,3',4,4'-biphenyl tetracarboxylic dianhydride ("BPDA"), bicyclic [2.2.2]oct-7-ene-2,3,5,6-tetracarboxylic dianhydride ("BTDA"), 3,3',4,4'-diphenylsulfone tetracarboxylic dianhydride ("DSDA"), 4,4'-(hexafluoroisopropylidene)diphthalic anhydride ("6FDA"), 4,4'-oxydiphthalic anhydride ("ODPA"), pyromellitic dianhydride ("PMDA"), 4-(2,5-dioxotetrahydrofuran-3-yl)-1,2,3,4-tetrahydronaphthalene-1,2-dicarboxylic anhydride ("DTDA"), and the like, but is not limited thereto. These may be used singularly or as a mixture of two or more compounds.

The dianhydride compound and the diamine compound may be included in a mole ratio of about 1:0.01 to about 1:1, for example about 1:0.1 to about 1:0.5.

The dianhydride compound and the first diamine compound may be included in a mole ratio of about 1:0.01 to about 1:1. Within the range, the compounds may be included in a mole ratio of about 1:0.01 to about 1:0.4.

The composition may further include an organic solvent. The organic solvent may be any solvent that dissolves the diamine compound and the dianhydride compound without limitation, and may be selected from, for example, dimethylsulfoxide; N-methyl-2-pyrrolidone; N,N-dimethylformamide ("DMF"); N,N-dimethylacetamide ("DMAc"); N-methylformamide ("NMF"); alcohols such as methanol, ethanol, 1-propanol, 2-propanol, 2-methyl-1-butanol, and 2-methyl-2-butanol; acyclic or cyclic esters such as methyl acetate, ethyl acetate, and γ-butyrolactone, acyclic or cyclic ketones such as cyclohexanone, 3-hexanone, 3-heptanone, 3-octanone, acetone, and methyl ethyl ketone; acyclic or cyclic ethers such as tetrahydrofuran ("THF"); diethyl ether, methyl tert-butyl ether, 1,4-dioxane, chlorinated solvents such as dichloromethane, carbon tetrachloride, and trichloroethane; or a combination thereof.

The dianhydride compound and the diamine compound may be polymerized to form a polymer.

The polymer may be, for example, polyamic acid, a polyimide, or a combination thereof.

The polymer may include, for example, a repeating unit represented by the following Chemical Formula 3, a repeating unit represented by the following Chemical Formula 4, or a combination thereof.

Chemical Formula 3

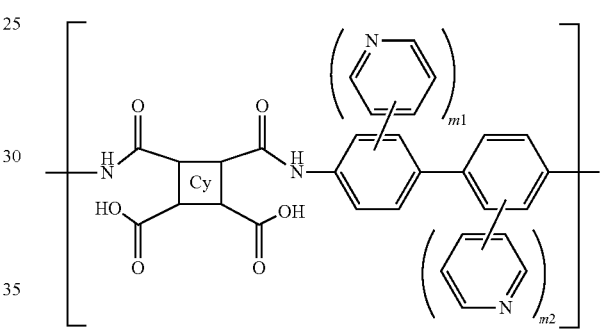

Chemical Formula 4

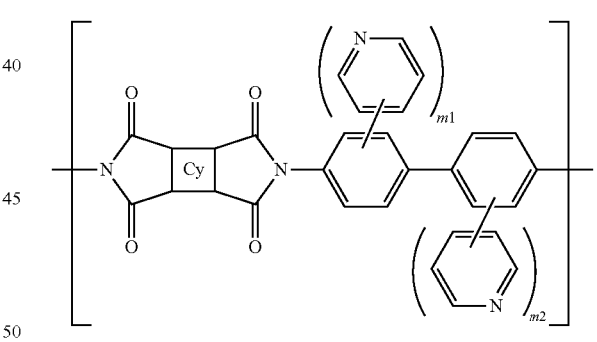

In the above Chemical Formula 3 or 4, Cy, m1, and m2 are the same as described above.

Since the polymer includes a moiety derived from the first diamine compound, heteroatoms of the heteroaryl group may form a secondary bond such as a van der Waals bond and control thermal motion of the polymer as described above. Accordingly, thermal stability is increased, while shrinkage/expansion due to heat is decreased.

In addition, a moiety derived from the first diamine compound may form a bulky side chain due to the heteroaryl group, and thus may hinder stacking of molecules and limit formation of a charge transfer ("CT") complex and resultantly improve photo-transmittance in a short wavelength region.

Accordingly, transparency of the polymer may be increased.

Accordingly, thermal stability and transparency of the polymer are simultaneously improved.

The polymer may be prepared by, for example, mixing the above diamine compound, a dianhydride compound, and a solvent, primarily polymerizing the mixed solution, and secondarily polymerizing the primarily polymerized product.

The primary polymerization may be performed at, for example, about 0 to about 100° C., for example, about 20° C. to about 80° C., for about 1 to about 24 hours, for example, for about 2 to about 18 hours, and thus the polymer may be present as a polyamic acid by the primary polymerization.

The secondary polymerization may be preformed, for example, at about 0 to about 180° C., for example, at about 20° C. to about 140° C. for about 6 to about 120 hours, for example, for about 12 to about 60 hours, and thus the polymer may be present as a polyimide or a mixture of the polyamic acid and polyimide due to the secondary polymerization.

As described above, the first diamine compound includes an aromatic group substituted with a heteroaryl group, and as such, needs no separate imidization catalyst such as, for example, pyridine during the polymerization. Thus a negative effect of the imidization catalyst and further improve transparency of the polymer may be prevented.

The polymer may be formed into a polymer film. The polymer film may be formed, for example, through a solution process such as spin coating, slit coating, inkjet printing, or a roll-to-roll process.

The polymer film may be used in a substrate, an insulation layer, an optical film, a semiconductor for a display device and a device packaging material, an adhesive film, a multi-layered FPC, a tape, and the like.

The polymer film is applied to a substrate for a display device and thus provides a flexible display device.

Hereinafter, application examples are described referring to drawings when the polymer film is a substrate for a display device.

FIG. 1 is a cross-sectional view of a liquid crystal display ("LCD") according to an embodiment.

Referring to FIG. 1, the liquid crystal display ("LCD") 100 includes a first polymer substrate 110 and a second polymer substrate 130 facing each other, and a liquid crystal layer 120 interposed between the first and second polymer substrates 110 and 130.

The first and second polymer substrates 110 and 130 may be the above polymer film.

A thin film transistor (not shown) and a first electric field generating electrode (not shown) connected thereto may be formed on the first polymer substrate 110, and a color filter (not shown) and a second electric field generating electrode (not shown) may be formed on the second polymer substrate 130. However, the color filter is not limited thereto and may be formed on the first polymer substrate 110, and the first and second electric field generating electrodes may be formed on the first polymer substrate 110.

The liquid crystal layer 120 may include a plurality of liquid crystal molecules. The liquid crystal molecules may have positive or negative dielectric anisotropy. When the liquid crystal molecules have positive dielectric anisotropy, the long axes of the liquid crystal molecules are arranged almost parallel to the surface of the first and second polymer substrates 110 and 130 when no electric field is applied thereto, but they may be almost perpendicular to the surface of the first and second polymer substrates 110 and 130 when an electric field is applied thereto. On the contrary, when the liquid crystal molecules have negative dielectric anisotropy, the long axes of the liquid crystal molecules are arranged almost perpendicular to the surface of the first and second polymer substrates 110 and 130 when no electric field is applied thereto, but they may be almost parallel to the surface of the first and second polymer substrates 110 and 130 when an electric field is applied thereto.

Figure 2:
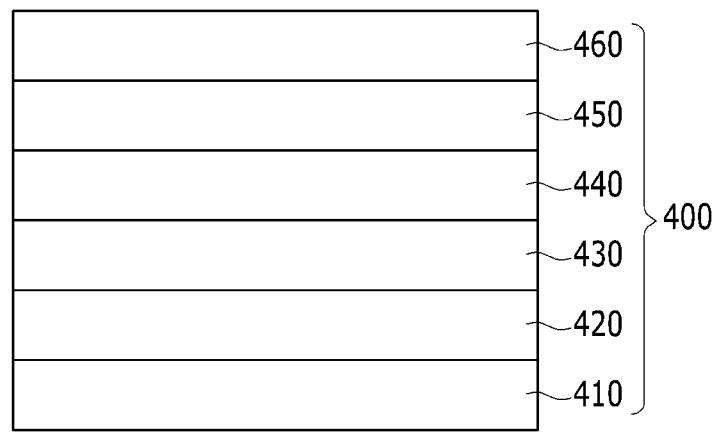
FIG. 2 is a cross-sectional view showing an organic light emitting diode ("OLED") according to an embodiment.

FIG. 2 is a cross-sectional view of an organic light emitting diode ("OLED") display according to an embodiment.

Referring to FIG. 2, an organic light emitting diode ("OLED") 400 includes a polymer substrate 410, a lower electrode 420, an organic emission layer 430, an upper electrode 440, an encapsulation substrate 450, and a polarizing film 460.

The polymer substrate 410 may be the above polymer film.

One of the lower electrode 420 and the upper electrode 440 is an anode, and the other is a cathode. The anode is an electrode into which holes are injected, and it may be formed of a transparent conductive material having a high work function and through which emitted light may pass, for example, ITO or IZO. The cathode is an electrode into which electrons are injected, and it may be formed of a conductive material having a low work function and that does not affect an organic material, for example, aluminum (Al), calcium (Ca) and barium (Ba).

The organic emission layer 430 includes an organic material that may emit light when a voltage is applied to the lower electrode 420 and the upper electrode 440.

An auxiliary layer (not shown) may be further included between the lower electrode 420 and the organic emission layer 430 and between the upper electrode 440 and the organic emission layer 430. The auxiliary layer may include a hole transport layer, a hole injection layer, an electron injection layer, and an electron transport layer in order to achieve a balance between electrons and holes.

The encapsulation substrate 450 may be made of glass, a metal, or a polymer, and seals the lower electrode 420, the organic emission layer 430, and the upper electrode 440 and prevents external moisture and/or oxygen from inflowing.

The polarizing film 460 may be disposed at a light-emitting side. For example, for a bottom emission structure that light emits from the polymer substrate 410, the polarizing film 460 may be disposed outside of the polymer substrate 410, while for a top emission structure light emits from the encapsulation substrate 450, the polarizing film 460 may be disposed outside of the encapsulation substrate 450. The polarizing film 460 may prevent reflection of externally inflowing light and improve visibility.

Hereinafter, the present disclosure is illustrated in more detail with reference to examples. However, these examples are exemplary, and the present disclosure is not limited thereto.

Synthesis Example

Reaction Scheme 1

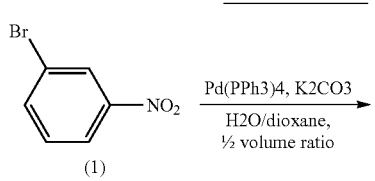

-continued

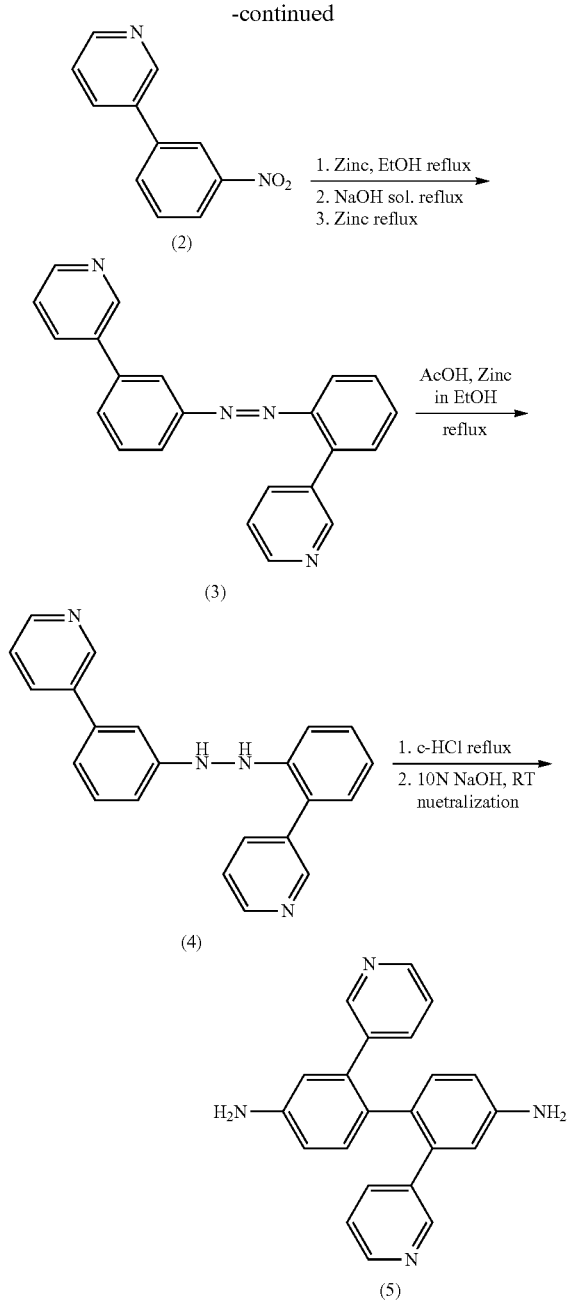

First Step 350 g of 3-bromonitrobenzene compound (1), 220 g of pyridine 3-boroxine hydrate, 4,100 g of tetrakis(triphenylphosphine)palladium (Pd(PPh$_3$)$_4$), 600 g of potassium carbonate (K$_2$CO$_3$), 900 ml of distilled water, and 1.8 L of dioxane are put in a flask and then refluxed and agitated under a nitrogen atmosphere for 21 hours. Subsequently, the reaction solution is filtered with a celite pad, and 800 ml of ethyl acetate and 800 ml of distilled water are added thereto to separate an organic layer from a water layer. The organic layer is then extracted by adding 1.2 L of 1 N HCl thereto. The water layer is distillated by using a 5 N NaOH aqueous solution, and is then extracted three times with 800 ml of ethyl acetate, dehydrated with Na$_2$SO$_4$, and concentrated under a reduced pressure to remove a solvent. Ethyl acetate and n-hexane are then added to the solid concentrated under reduced pressure to prepare a slurry, and the slurry is filtered. Subsequently, the slurry is dried at 55° C., obtaining 209.5 g of 3-(3-nitrophenyl)pyridine compound (2).

Second Step 203 g of 3-(3-nitrophenyl)pyridine, 800 g of zinc, and 4.0 L of ethanol are put in a flask and heated to 70° C. A solution prepared by dissolving 98 g of sodium hydroxide (NaOH) in 700 mL of distilled water is then added to the reaction solution, and the mixture is agitated at 70° C. for 5 hours. Subsequently, 200 g of zinc is additionally added to the reaction solution, and the mixture is agitated for one more hour at the same temperature. The reaction solution is filtered when hot, and then washed with a mixed solvent of 1 L of acetone and 3 L of ethanol. Subsequently, 4.0 L of distilled water is added to the filtered solution, and the mixture is cooled to 5° C., agitated for 30 minutes, and filtered, obtaining compound (3).

Third Step

Compound (3), 1 L of acetic acid, 220 g of zinc, and 1.5 L of ethanol are put in a flask, heated to 80° C., and agitated for 3 hours. The reaction solution is filtered when hot, 2.0 L of distilled water is added thereto, and the mixture is cooled to 5° C. The cooled reaction solution is agitated for 30 minutes and then filtered, obtaining compound (4).

Fourth Step

Compound (4) and 2.0 L of strong sulfuric acid (c-HCl) are put in a flask and then refluxed and agitated for 5 hours. The reaction solution is then cooled to room temperature and filtered. Subsequently, 10 N sodium hydroxide (NaOH) is used to adjust pH of the filtered solution to neutral. The solution is then cooled to 5° C., agitated for 30 minutes, and filtered. Subsequently, 2 L of methanol is added to the filtered solid, and the mixture is refluxed and agitated for 2 hours and then cooled to 5° C. The cooled resultant is then agitated for 30 minutes and filtered and dried at 55° C. for one day, obtaining 48.4 g of a diamine compound 5 represented by the following Chemical Formula A.

Chemical Formula A

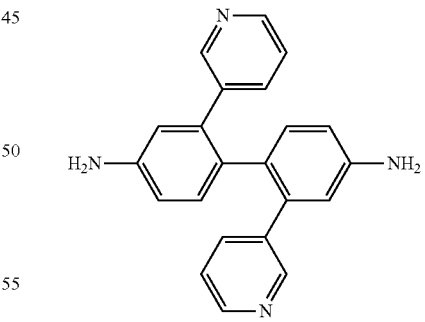

Examination of Synthesized Product

The structure of the diamine compound represented by Chemical Formula A is examined through $^1$H NMR.

The results are provided as follows.

$^1$H-NMR (600 MHz, DMSO, ppm): δ 8.24 (m, 2H, Ar—H), δ 7.64 (d, 2H, Ar—H), δ 7.02-7.04 (m, 4H, Ar—H), δ 6.82 (d, 2H, Ar—H), δ 6.62 (d, 2H, Ar—H), 6 6.31 (d, 2H, Ar—H), δ 5.13 (s, 4H, —NH$_2$)

EXAMPLES

Example 1

The diamine compound represented by Chemical Formula A according to a synthesis example, the dianhydride compound represented by the following Chemical Formula B, and the diamine compound represented by the following Chemical Formula C are mixed, preparing a composition including 18 wt % of a solid of dimethylacetamide ("DMAc").

Herein, the dianhydride compound, the diamine compound represented by Chemical Formula A, and the second diamine compound represented by Chemical Formula C are mixed in a mole ratio of 1:0.05:0.95.

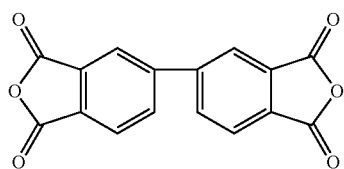

Chemical Formula B

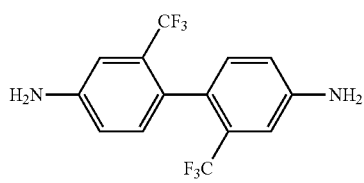

Chemical Formula C

Subsequently, the composition is polymerized at 20° C. for 48 hours. Following this, the composition is spin coated to form an about 10 micrometers ("μm") thick film at a speed ranging from about 1000 to 1500 rpm on a substrate. The coated substrate is pre-baked at 80° C. for 1 hour, heated at a speed of 3° C./min, and heat-treated at 300° C. for 1 hour, forming a polyimide film.

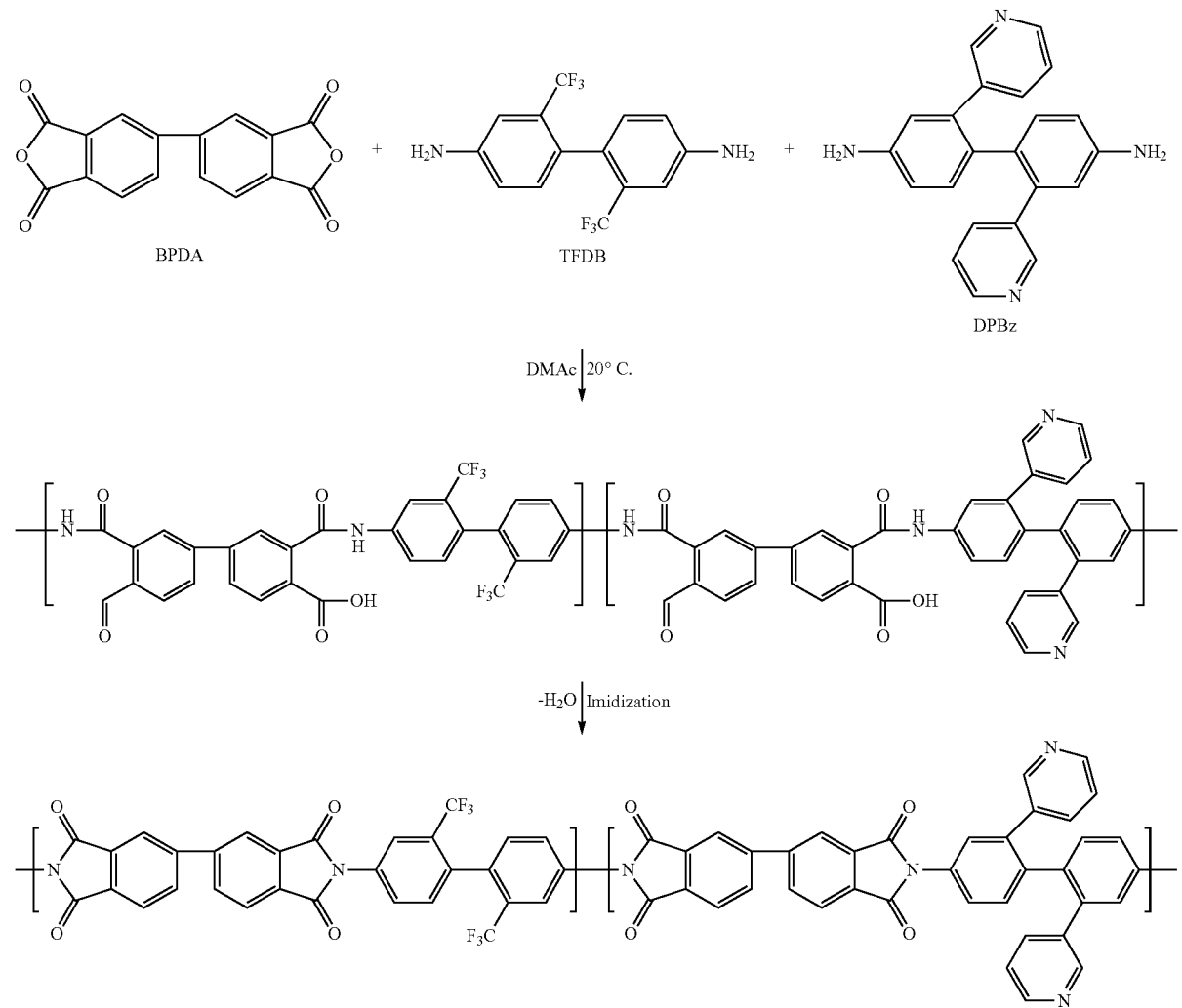

Reaction Scheme 2

Example 2

A polyimide film is formed according to the same method as in Example 1, except for preparing a composition by mixing the dianhydride compound, the diamine compound represented by Chemical Formula A, and the second diamine compound represented by Chemical Formula C in a mole ratio of 1:0.10:0.90.

Example 3

A polyimide film is formed according to the same method as in Example 1, except for preparing a composition by mixing the dianhydride compound, the diamine compound represented by Chemical Formula A, and the second diamine compound represented by Chemical Formula C in a mole ratio of 1:0.20:0.80.

Comparative Example 1

A polyimide film is formed according to the same method as in Example 1, except for preparing a composition by using no diamine compound represented by Chemical Formula A and mixing the dianhydride compound and the second diamine compound represented by Chemical Formula C in a mole ratio of 1:1.

Evaluation 1

Transmittance of the polyimide films according to Examples 1 to 3 and Comparative Example 1 is evaluated.

The transmittance is evaluated by measuring transmittance at a short wavelength and an average transmittance over the entire visible ray spectrum with a spectrophotometer made by Konica Minolta.

The results are provided in Table 1.

TABLE 1

|  | Transmittance (@430 nm, %) | Average transmittance (400-800 nm, %) |
|---|---|---|
| Example 1 | 83.8 | 87.2 |
| Example 2 | 83.0 | 87.1 |
| Example 3 | 84.5 | 87.4 |
| Comparative Example 1 | 80.2 | 87.3 |

Referring to Table 1, the polyimide films according to Examples 1 to 3 show improved photo-transmittance at a short wavelength (@430 nm) compared with the polyimide film according to Comparative Example 1. These polyimide films show improved effects compared with a conventional polyimide film having deteriorated transparency due to low transmittance at a short wavelength region.

Evaluation 2

Thermal stability of the polyimide films according to Examples 1 to 3 and Comparative Example 1 is evaluated.

The thermal stability is evaluated by measuring a decomposition temperature ("$T_d$") at which 0.5 wt % of the total weight of the polyimide films decreases by using a thermogravimetric analyzer (TGA Q5000, TA instruments) (heating rate: 10° C./min).

The results are provided in Table 2.

TABLE 2

|  | Decomposition temperature (Td) (@ weight loss of 0.5 wt %, ° C.) |
|---|---|
| Example 1 | 522.6 |
| Example 2 | 520.6 |
| Example 3 | 526.3 |
| Comparative Example 1 | 511.6 |

Referring to Table 2, 0.5 wt % of the total weight of the polyimide films according to Examples 1 to 3 is decomposed at a higher temperature than the polyimide film according to Comparative Example 1 due to outgassing. Accordingly, the polyimide films according to Examples 1 to 3 show improved thermal stability compared with the polyimide film according to Comparative Example 1.

Evaluation 3

Coefficients of thermal expansion ("CTE") of the polyimide films according to Examples 1 to 3 and Comparative Example 1 are evaluated.

The coefficients of thermal expansion ("CTE") are evaluated by using a thermomechanical analyzer ("TMA") (5° C./min, pre-load: 10 mN, TMA 2940, TA Instruments).

The results are provided in Table 3.

TABLE 3

| | Coefficients of thermal expansion (CTE, ppm/° C.) | | |
|---|---|---|---|
| | 50-150° C. | 50-200° C. | 50-300° C. |
| Example 1 | 9.1 | 11.8 | 17.8 |
| Example 2 | 8.2 | 10.4 | 15.2 |
| Example 3 | 8.6 | 11.0 | 16.8 |
| Comparative Example 1 | 19.2 | 19.7 | 24.6 |

Referring to Table 3, the polyimide films according to Examples 1 to 3 show lower coefficients of thermal expansion than those of the polyimide film according to Comparative Example 1.

Accordingly, the polyimide films according to Examples 1 to 3 show improved transmittance at a short wavelength, and simultaneously have improved thermal stability and thermal expansion characteristics.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A composition, comprising
at least one diamine compound and
at least one dianhydride compound,
wherein the diamine compound comprises a compound represented by Chemical Formula 1:

Chemical Formula 1

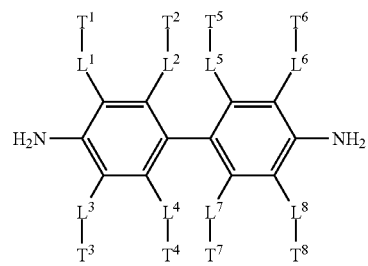

wherein, in Chemical Formula 1,
$T^1$ to $T^8$ are each independently hydrogen, a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group, at least one of $T^1$ to $T^8$ is a substituted or unsubstituted C2 to C30 heteroaryl group, and $L^1$ to $L^8$ are independently a single bond, a substituted or unsubstituted C1 to C20 alkylene group, a substituted or unsubstituted C3 to C20 cycloalkylene group, a substituted or unsubstituted C2 to C30 heterocycloalkylene group, a substituted or unsubstituted C6 to C30 arylene group, $SiR^aR^b$—, —$(Si=O)_p$—, —$NR^cR^d$—, or a combination thereof, wherein $R^a$ to $R^d$ are each independently hydrogen or a substituted or unsubstituted C1 to C20 alkyl group, and p is 1 to 20.

2. The composition of claim 1, wherein the compound represented by Chemical Formula 1 is represented by Chemical Formula 2:

Chemical Formula 2

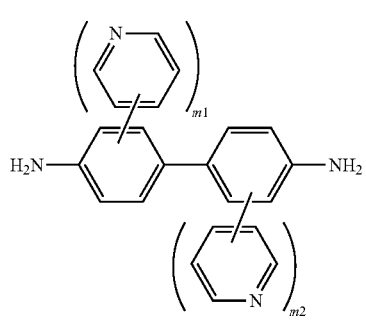

wherein, in Chemical Formula 2, m1 and m2 are each independently 0 or 1, provided that m1 and m2 are not simultaneously 0.

3. The composition of claim 2, wherein the compound represented by Chemical Formula 2 comprises at least one selected from compounds listed in Group 1:

Group 1

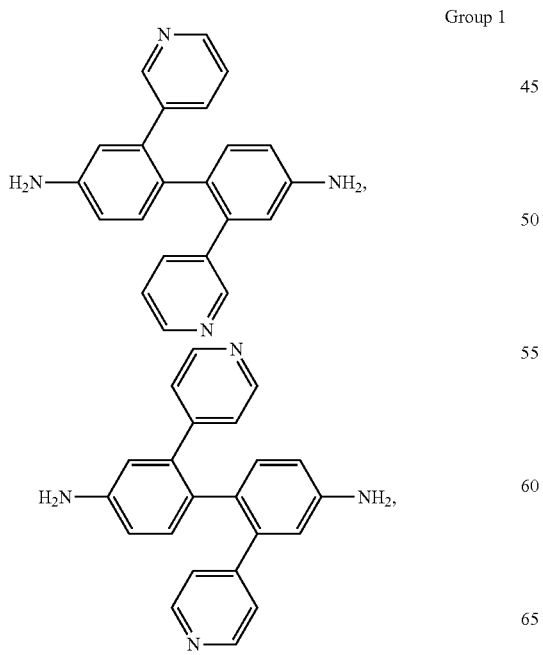

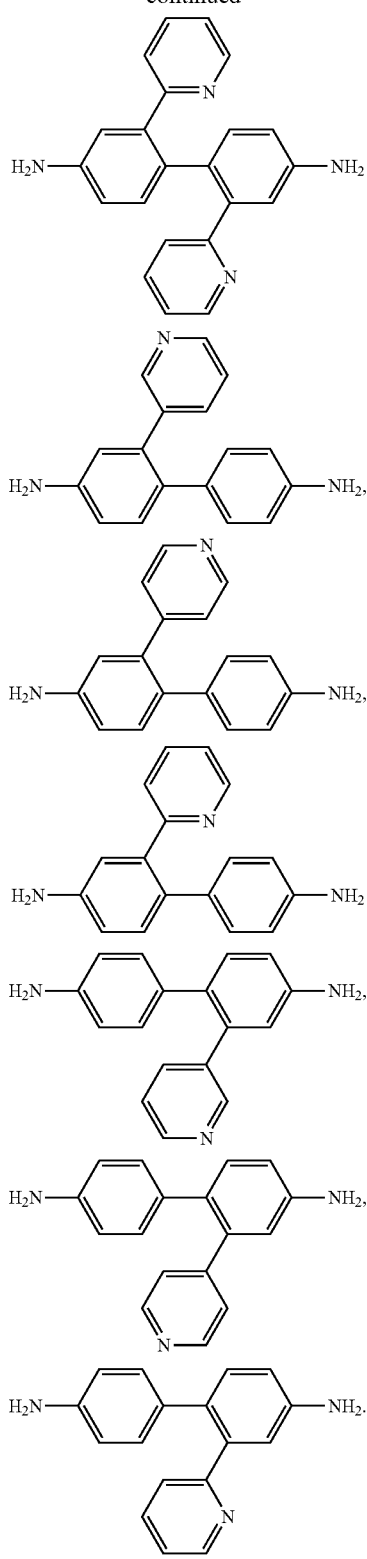

4. The composition of claim 1, wherein the diamine compound further comprises at least one compound represented by Chemical Formula 5:

Chemical Formula 5

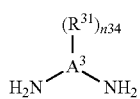

wherein, in Chemical Formula 5,

A³ is a substituted or unsubstituted group derived from a C1 to C20 alkane, a C6 to C30 arene, a C3 to C30 heteroarene, a C3 to C30 cycloalkane, a C3 to C30 heterocycloalkane, or a combination thereof, R³¹ is hydrogen, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C2 to C15 heteroaryl group, or a combination thereof, n³⁴ is an integer ranging from 0 to 10, provided that n34+2 is equal to the bond valency of A³.

5. The composition of claim 1, wherein the compound represented by Chemical Formula 1 is included in a ratio of about 0.01 to about 1 mole based on a total of 1 mole of the dianhydride compound.

6. The composition of claim 5, wherein the compound represented by Chemical Formula 1 is included in a ratio of about 0.01 to 0.4 moles based on 1 mole of the dianhydride compound.

7. A polymer film comprising a polymer, wherein the polymer is a polymerization product of the composition of claim 1.

8. The polymer film of claim 7, wherein the polymer is a polyamic acid, a polyimide, or a combination thereof.

9. The polymer film of claim 7, wherein the polymer comprises a repeating unit represented by Chemical Formula 3, a repeating unit represented by Chemical Formula 4, or a combination thereof:

Chemical Formula 3

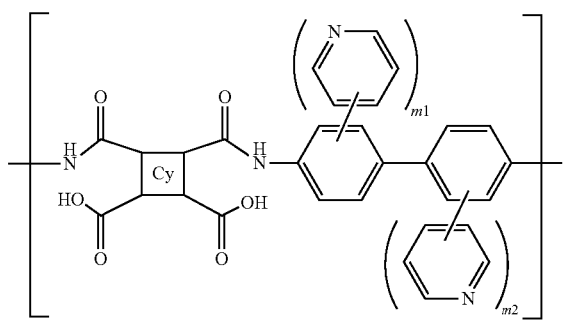

Chemical Formula 4

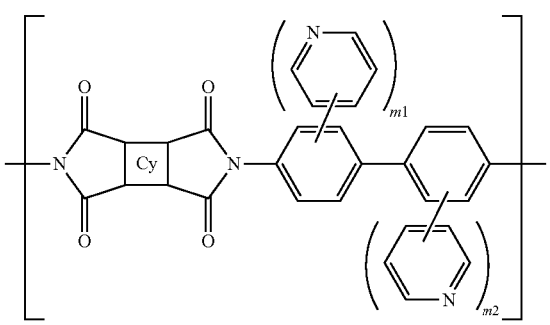

wherein, in Chemical Formula 3 or 4,

Cy is a group comprising a substituted or unsubstituted C3 to C20 cycloalkyl group, a substituted or unsubstituted C3 to C20 heterocycloalkyl group, a substituted or unsubstituted C6 to C20 aryl group, a substituted or unsubstituted C3 to C20 heteroaryl group, or a combination thereof, m1 and m2 are each independently 0 or 1, provided that m1 and m2 are not simultaneously 0.

10. A display device comprising the polymer film of claim 7.

11. The display device of claim 10, wherein the polymer film is a substrate.

12. The display device of claim 11, further comprising a thin film transistor, a liquid crystal device, an organic light emitting diode, or a combination thereof disposed on a side of the polymer film.

13. The composition of claim 1, wherein the dianhydride compound is represented by Chemical Formula 6:

Chemical Formula 6

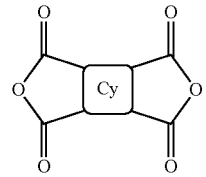

wherein, in Chemical Formula 6,

Cy is a moiety including a C3 to C20 cycloalkyl group, a C3 to C20 heterocycloalkyl group, a C6 to C20 aryl group, a C3 to C20 heteroaryl group, or a C3 to C20 cycloalkyl group, a C3 to C20 heterocycloalkyl group, a C6 to C20 aryl group, a C3 to C20 heteroaryl group each substituted with at least one substituent selected from the group consisting of a halogen atom, a hydroxy group, a C1 to C20 alkoxy group, a cyano group, carboxyl group, a C1 to C20 ester group, a ketone group, a C1 to C20 alkyl group, a C2 to C20 alkenyl group, a C2 to C20 alkynyl group, a C1 to C20 aryl group, and a C1 to C20 heteroaryl group.

14. The composition of claim 13, wherein the dianhydride compound is at least one selected from the group consisting of 3,3',4,4'-biphenyl tetracarboxylic dianhydride, bicyclic [2.2.2]oct-7-ene-2,3,5,6-tetracarboxylic dianhydride, 3,3',4, 4'-diphenylsulfone tetracarboxylic dianhydride, 4,4'-(hexafluoroisopropylidene)diphthalic anhydride, 4,4'-oxydiphthalic anhydride, pyromellitic dianhydride, and 4-(2, 5-dioxotetrahydrofuran-3-yl)-1,2,3,4-tetrahydronaphthalene-1,2-dicarboxylic anhydride.

* * * * *